United States Patent [19]
Minuth

[11] Patent Number: 5,665,599
[45] Date of Patent: Sep. 9, 1997

[54] CHAMBER FOR CULTIVATING CELLS

[76] Inventor: Will Minuth, Starenstrasse 2, D-93077 Bad Abbach, Germany

[21] Appl. No.: 561,663

[22] Filed: Nov. 22, 1995

[30] Foreign Application Priority Data

Dec. 1, 1994 [DE] Germany ............... 44 42 797.2
Dec. 9, 1994 [DE] Germany ............... 44 43 902.4

[51] Int. Cl.$^6$ ................................... C12M 1/22
[52] U.S. Cl. ................. 435/288.3; 435/288.4; 435/297.5; 435/305.1; 435/305.4; 359/398
[58] Field of Search ................. 435/288.3, 288.4, 435/288.7, 297.5, 305.1–305.4, 808, 297.2; 422/102; 359/398, 395; 356/244, 246

[56] References Cited

U.S. PATENT DOCUMENTS

| | | | |
|---|---|---|---|
| 2,940,360 | 6/1960 | Carter | 359/398 |
| 2,942,520 | 6/1960 | Rose | 359/398 |
| 3,726,597 | 4/1973 | Dvorak et al. | 359/398 |
| 5,414,556 | 5/1995 | Focht | 359/398 |

FOREIGN PATENT DOCUMENTS

| | | | |
|---|---|---|---|
| 4-186311 | 7/1992 | Japan | 359/398 |
| 248900 | 7/1969 | U.S.S.R. | 435/305.1 |
| 1594211 | 9/1990 | U.S.S.R. | 435/297.2 |

Primary Examiner—William H. Beisner
Attorney, Agent, or Firm—Hoffman, Wasson & Gitler

[57] ABSTRACT

A multipart chamber for cultivating cells for observing long-term cell cultures. Extremely small distances can be achieved between the objective of the microscope and the planes inside the chamber resulting for cell observation. Further, the chambers can have conduits attached thereto for feeding or draining liquid or gaseous materials therein.

16 Claims, 2 Drawing Sheets

CHAMBER FOR CULTIVATING CELLS

BACKGROUND OF THE INVENTION

The invention relates to a chamber for cultivating cells and, in particular, to a chamber that makes it possible microscopically to observe long-term cell cultures.

Chambers for cultivating cells are known, especially those in which such a chamber is divided into two sectional chambers or subspaces, between which a carrier for the cells to be cultivated (cell carrier) can be placed. In addition, conduits can be placed in each chamber, so it is possible to feed and drain gaseous or liquid mediums.

The object of the present invention is to provide a chamber that makes it possible microscopically to observe or investigate cells on a cell carrier and/or in subspaces of the chamber, with high magnification.

SUMMARY OF THE INVENTION

To achieve this object, a chamber is made which includes a multipart housing, each part having a hole or recess arranged in axial alignment when the housing is closed, and each of which forms a part of an interior of the chamber, and in at least one recess a sealing ring surrounding the axis of this recess is provided, a sealing ring that lies against the inner surface of a disk that closes the interior of the chamber to the outside and forms an observation window, wherein the disk is supported, on the outer surface facing away from the interior of the chamber or on the contact surface of the sealing ring, directly opposite a holding plate that has an opening that opposes the observation window and is removably attached to the housing part.

The invention has the advantage that, with observation and investigation with optical microscopes, extremely small distances can be achieved between the objective lens of the microscope being used and the planes inside the chamber that are of interest. In particular, the inner surface of the disk occluding the interior of the chamber or the plane of a cell carrier installed in the chamber can be observed. These small distances result on the one hand from the fact that the sealing ring simultaneously effects a sealing in the area of the cell carrier or a carrying ring provided there, and on the other hand from having the cell carrier, placed in the area of the disk. It is essential that, with this design, the thickness of the disk be kept extremely small, since the disk, on its side opposite the sealing ring, is supported directly on the support plate. The restraining or compressive forces act exclusively perpendicular to the plane of this disk, and therefore it is essential no forces or moments are present that would cause a breaking of the disk. The same advantages also apply to the use of electron microscopes, laser microscopes, and to observation and measuring devices and systems, that operate ultrasonically or with infrared light.

Because of the type of fastening achieved, the disk is replaceable. Disks suitable for respective applications and disks made of optimal materials can be selected, as desired.

In the invention, the chamber can be opened by removing the holding plate. In the open state, the chamber can then be placed, e.g., with the opening, on surgical operating surfaces and specifically perfusion (feeding and draining of media through the conduits of the chamber) can further be performed. In doing so, the cultivated cell material has the opportunity optimally to grow together with body tissue.

BRIEF DESCRIPTION OF THE DRAWINGS

The object is explained in further detail based on an embodiment using the figures.

DETAILED DESCRIPTION OF THE INVENTION

Figure 1:
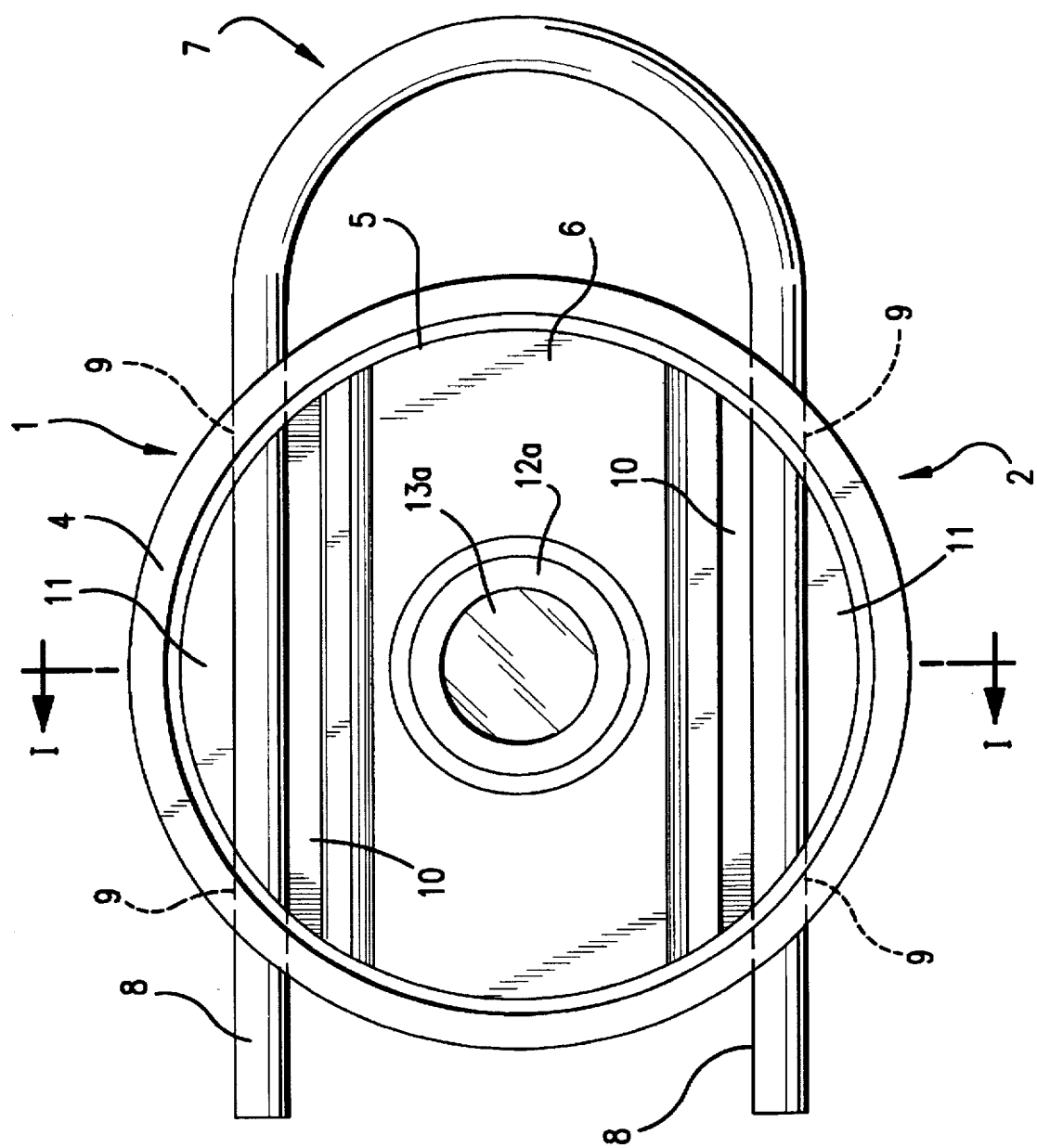
FIG. 1 is a top view of a microscope chamber according to the invention.

The chamber designated in general by 1 in the figures, which is used to cultivate cells, can also be used as a perfusion chamber. The chamber makes it possible to perform analytic evaluation and observation with known devices and systems. More particularly, the chamber can be considered a microscope chamber, and include a disk-shaped housing 1 made of a suitable plastic.

Housing 1 is made in two parts and has a lower, bowl-type housing part 2 that is produced integrally with a bottom 3 and a flat edge 4. Edge 4 encompasses a circular opening 5 into which housing part 6, shaped essentially like a circular disk, is inserted.

To lock housing part 6 in opening 5 of housing part 1, a bracket 7 is used. The bracket 7 is bent from a length of a metal rod and has two parallel legs 8. The bracket 7 is guided, with these legs 8, in each case through holes 9 of edge 4 so that the plane of bracket 7 lies about parallel to the plane of the underside of bottom 3 and each leg 8, in the area of a recess 10. The legs 8 lie against a surface 11 of housing part 6 that faces away from bottom 3. Because legs 8 are beveled into a wedge shape on their sides that lie against surface 11, housing part 6 lies, with its underside 6', pressed against bottom surface 5' of opening 5.

The housing part is provided, on bottom 3, with a central, continuous opening 12 that forms, with a section 12', a part of the interior of the microscope chamber and exhibits, toward the underside of the bottom, a section 12" that has a larger diameter compared to section 12'. Both sections 12' and 12" have circular cross sections. Into section 12" is inserted a thin disk 13 that forms the bottom of the interior of the chamber and consists of a transparent or radiolucent material, e.g., glass. The thickness of disk 13, which forms an observation window, is extremely thin to achieve extremely small optical heights and thus the desired high magnification during observation with an inverse microscope, i.e., from below. The objective lens of the inverse microscope is indicated by 14.

The inner side of disk 13 lies against a sealing ring 15 (O-ring) that is inserted into section 12' of hole 12. With the side facing away from disk 13, sealing ring 15 is supported against a ring 16 on which a cell carrier 17 is held.

A seal 18 that consists, for example, of silicone rubber or another suitable material, is made as a flat ring, and lies against the underside of disk 13 in the area of the edge of this disk. Disk 13 is held by a holding plate 19 that is made as a metal plate and is connected to bottom 3 of housing part 2 in a suitable way, for example by screwing. Holding plate 19 has a circular opening 20 that is placed in axial alignment with lengthwise axis L of hole 12 and exposes the observation window formed by the disk and whose diameter is somewhat larger than the inner diameter of sealing ring 15 but smaller than the arithmetic means between the inner diameter and the outer diameter of sealing ring 15, so that, on the underside of housing part 2, glass plate 13 is held above seal 18 by holding plate 19, where sealing ring 15 lies against the top side of this disk, so that restraining or compressive forces acting in the direction of the thickness of disk 13 act on the disk. No forces on the moments that could cause a breaking of thin disk 13.

In the same way as lower housing part 2, upper housing part 6 is provided with a hole 12a that lies, when housing 1 is closed, with its axis aligned with lengthwise axis L of housing part 2. Into hole 12a which, in turn, exhibits a section 12a' corresponding to section 12' and a section 12a" corresponding to section 12", is inserted a sealing ring 15a that corresponds to sealing ring 15 and that lies, below, against ring 16 and, above, against the lower side of disk 13a. Disk 13a is held on the top side again in the same way as it was described for disk 13, by a holding plate 19a and a seal 18a between them, so that as far as disks 13, 13a, their fastening and seals 15, 15a are concerned, there is a structure that is made symmetrical to central plane M of ring 16. The lower side of disk 13a forms the upper boundary of the interior of the chamber.

Figure 2:
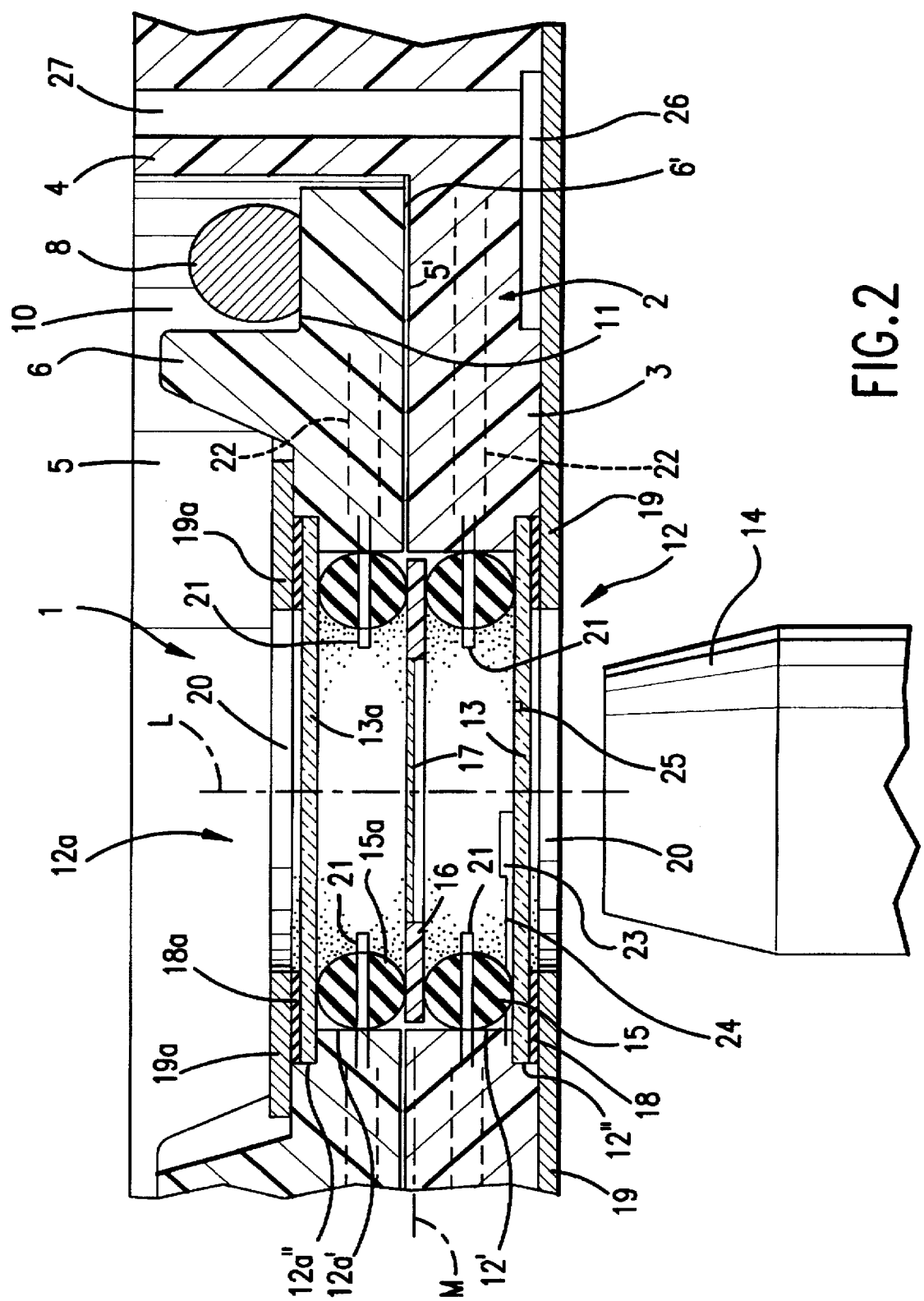
FIG. 2 is a simplified enlarged representation taken along line I—I of FIG. 1.

As FIG. 2 further shows, conduits 21, which extend radially with respect to lengthwise axis L, are guided through seals 15 and 15a and empty into conduits 22 in housing part 2 or 6. They make it possible to feed or drain liquid or gaseous media into or out of the subspaces formed above and below cell carrier 17. This also contributes to the flat structural shape thus achieving small optical lengths. Further, the seals are secured by conduits 21 when the chamber is opened.

Numeral 23 designates an electrical sensor that is attached on the top side or inner surface of disk 13. Generally, the multiwire electrical connection 24 of this sensor 23 is guided between sealing ring 15 and the inner surface of disk 13 out of the interior of the chamber. Sensor 23 makes it possible to have a connection between optical and electrical measuring or observing. It is possible to provide, for example, instead of electrical sensor 23, and/or in addition to it, an optical sensor. Disk 13 can further be provided, on its inner surface, with indentations 25, for example in the form of troughs or grooves, that are used as markings to facilitate microscopic observations or to facilitate, growing cells or to control the direction of the spreading of the cells.

The replacement of disks 13 and 13a is a simple process that can be undertaken without problems. Further, the glass disks can be replaced with disks made of another suitable material, e.g., permeable disks or disks made of a material suitable as a substrate for an implant, for example, for cartilage or bone cells. Further, the disks 13 and 13a can be membranes, for example, gas-permeable membranes or membranes that make it possible for the cells to grow through them. The thickness of disks 13 and 13a is on the order of about 0.1 mm. In this way, the extremely small optical distances between objective lens 14, provided for inverse observation, and the inner surface of disk 13 are achieved. Further, very small distances between objective lens 14 and the plane of cell carrier 17, are achieved. Thus long-term cultures (e.g., as bone cells) can be observed for a given time, and then placed at the site of a fracture of an extremity of the human body.

For example, hormone-producing cells can be cultivated with the chamber and then transferred after a certain time.

It is possible to heat the chamber or the interior formed by sections 12' and 12a' by holding plates 19 and/or by closing bracket 8.

In the embodiment represented, holding plate 19 extends over the entire underside of bottom 3. Plate 19 is held there either by screws or other mechanical fastening means or also by adhesion. A vacuum can also be used to fasten plate 19. In this case there is inserted, into the underside of bottom 3, a conduit 26 that is open toward this bottom and encompasses axis L concentrically, a conduit that can have applied to it, by connection 27, a vacuum that holds plate 19.

What is claimed is:

1. A microscope chamber for cultivating cells comprising:
   a multipart housing (1) with at least a first housing part (2) with a first recess (12) and a second housing part (6) with a second recess (12a);
   said first recess of said first housing part and said second recess of said second housing part arranged in axial alignment when said multipart housing is closed;
   said first housing part and said second housing part forming a portion of an interior of said microscope chamber;
   at least a first and a second sealing ring (15, 15a) each of which being positioned in said first recess (12) and said second recess (12a) and surrounding an axis of said first and second recess; first and second disks (13, 13a), each of which is provided on said first and second housing parts, which closes said interior of said microscope chamber to the outside and forms an observation window with said at least first and second sealing rings (15, 15a) resting against an inner surface of said first and second disks (13, 13a), with at least said first disk of said first housing part being supported on a surface facing away from an interior of said microscope chamber and being directly opposite to said first sealing ring (15) being supported on a holding plate (19);
   said holding plate having an opening (20) that exposes said observation window and is removably attached to said first and second housing parts; and
   a cell carrier ring (16) on which a cell carrier (17) is held, and which is positioned in between said at least first and second sealing rings (15, 15a), with said at least first and second sealing ring resting against said cell carrier ring (16) such that said interior of the chamber is divided into two separate part-chambers.

2. A microscope chamber as claimed in claim 1, wherein said cell carrier ring is made of elastic material.

3. A microscope chamber as claimed in claim 1, wherein said holding plate is a metal plate.

4. A microscope chamber as claimed in claim 1, further comprising at least one conduit for a liquid or gaseous medium guided through said at least first and second sealing ring.

5. A microscope chamber as claimed in claim 4, wherein said at least one conduit is tubular or slot-shaped.

6. A microscope chamber as claimed in claim 5, wherein said at least one conduit has a round or oval cross-section.

7. A microscope chamber as claimed in claim 1, wherein said first and second housing parts are made symmetrically with respect to holding and sealing of said at least one disk delimiting the interior of said chamber.

8. A microscope chamber as claimed in claim 1, wherein said first and second disks have indentations or markings on an inner surface.

9. A microscope chamber as claimed in claim 1, wherein at least one electrical and/or optical sensor is placed on an inner surface of said first and second disks.

10. A microscope chamber as claimed in claim 1, wherein said first and second disks consist of a permeable material.

11. A microscope chamber as claimed in claim 1, wherein said first and second disks are replaceable.

12. A microscope chamber as claimed in claim 1, wherein said holding plate is heated.

13. A microscope chamber as claimed in claim 1, wherein said interior of said chamber has a cylindrical cross section.

14. A microscope chamber as claimed in claim 1, wherein said interior of said chamber has a rectangular or square cross section.

15. A microscope chamber as claimed in claim 1, wherein said at least one holding plate is held on said first and second housing part by adhesion or by a vacuum.

16. A microscope chamber for cultivating cells comprising:

- a multipart housing (1) with at least a first housing part (2) with a first recess (12) and a second housing part (6) with a second recess (12a);
- said first recess of said first housing part and said second recess of said second housing part arranged in axial alignment when said multipart housing is closed;
- said first housing part and said second housing part forming a portion of an interior of said microscope chamber;
- at least a first and a second sealing ring (15, 15a) each of which being positioned in said first recess (12) and said second recess (12a) and surrounding an axis of said first and second recess; first and second disks (13, 13a), each of which is provided on said first and second housing parts, which closes said interior of said microscope chamber to the outside and forms an observation window with said at least first and second sealing rings (15, 15a) resting against an inner surface of said first and second disks (13, 13a), with at least said first disk of said first housing part being supported on a surface facing away from an interior of said microscope chamber and being directly opposite to said first sealing ring (15) being supported on a holding plate (19);
- said holding plate having an opening (20) that exposes said observation window and is removably attached to said first and second housing parts;
- said first housing part being provided with an opening (5) into which said second housing part (6) is inserted when said multipart housing is closed, said opening having a bottom and an edge (4) encompassing said opening (5);
- a locking bracket (7) bent from a length of a metal rod and having two parallel legs (8);
- holes (9) in said edge (4) encompassing said opening (5) for receiving said second housing part (6); and
- said legs of said locking bracket (7) being guided through said holes (9) such that said two parallel legs (8) lie against a surface side (11) of said second housing part (6) facing away from said bottom of said opening (5) of said first housing part (2).

* * * * *